(12) United States Patent
Bandman et al.

(10) Patent No.: US 6,416,755 B1
(45) Date of Patent: Jul. 9, 2002

(54) HUMAN BETA-ALANINE-PYRUVATE AMINOTRANSFERASE

(75) Inventors: Olga Bandman, Mountain View; Preeti Lal, Santa Clara; Neil C. Corley, Mountain View, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 144 days.

(21) Appl. No.: 09/593,722

(22) Filed: Jun. 13, 2000

Related U.S. Application Data

(62) Division of application No. 09/015,296, filed on Jan. 29, 1998, now Pat. No. 6,103,471.

(51) Int. Cl.[7] ............................ A61K 38/51; C12N 9/10; C12N 1/20; C12N 15/00; C07H 21/04
(52) U.S. Cl. ................... 424/94.5; 435/193; 435/252.3; 435/320.1; 536/23.2
(58) Field of Search .............................. 435/193, 252.3, 435/320.1; 536/23.2; 424/94.5

(56) References Cited

PUBLICATIONS

Stryer, L., *Biochemistry*, 3rd Edition, Chapter 21, W.H. Freeman and Company, New York (1988).

Kawasaki, S., et al., (GI 1944136), GenBank Sequence Database (Accession AB002584), National Center for Biotechnology Information, National Library of Medicine, Bethesda, Maryland.

Kawasaki, S., et al., (GI 1944135), GenBank Sequence Database (Accession AB002584), National Center for Biotechnology Information, National Library of Medicine, Bethesda, Maryland.

*Primary Examiner*—Tekchand Saidha
(74) *Attorney, Agent, or Firm*—Incyte Genomics, Inc.

(57) ABSTRACT

The invention provides a human beta-alanine-pyruvate aminotransferase (HAPA) and polynucleotides which identify and encode HAPA. The invention also provides expression vectors, host cells, antibodies, agonists, and antagonists. The invention also provides methods for treating or preventing disorders associated with expression of HAPA.

9 Claims, 7 Drawing Sheets

```
                                 9                  18                 27                 36                 45                54
5' CGC CCG CGC GGC GAC GTC TCC GCG AGG CGT CAC GGC ACC GAC TGA CGG CCA CCC 63                 72                 81                 90                 99                108
ACC ATG GCC GCA GAC CAG CGC CCG AAG GCC GAC ACC CTG GCC CTG AGG CAA CGG
     M   A   A   D   Q   R   P   K   A   D   T   L   A   L   R   Q   R 117                126                135                144                153                162
CTC ATC AGC TCT TCC TGC AGA CTC TTT TTT CCC GAG GAT CCT GTT AAG ATT GTC
 L   I   S   S   S   C   R   L   F   F   P   E   D   P   V   K   I   V 171                180                189                198                207                216
CGG GCC CAA GGG CAG TAC ATG TAC GAT GAA CAG GGG GCA GAA TAC ATC GAT TGC
 R   A   Q   G   Q   Y   M   Y   D   E   Q   G   A   E   Y   I   D   C 225                234                243                252                261                270
ATC AGC AAT GTG GCG CAC GTT GGG CTC AAC AGC CAC TGC CTC CTC GTG CAA GCA GCA
 I   S   N   V   A   H   V   G   L   N   S   H   C   L   L   V   Q   A   A 279                288                297                306                315                324
CAT GAG CAG AAC CAG GTG CTC AAC ACC AAC AGC CGG TAC CTG CAT GAC AAC ATC
 H   E   Q   N   Q   V   L   N   T   N   S   R   Y   L   H   D   N   I 333                342                351                360                369                378
GTG GAC TAT GCG CAG AGG CTG TCA GAG ACC CTG CCG GAG CAG CTC TGT GTG TTC
 V   D   Y   A   Q   R   L   S   E   T   L   P   E   Q   L   C   V   F
```

Figure 1A

```
     387       396       405       414       423       432
TAT TTC CTG AAT TCT GGG TCA GAA GCC AAT GAC CTG GCC CTG AGG CTG GCT CGC
 Y   F   L   N   S   G   S   E   A   N   D   L   A   L   R   L   A   R 441       450       459       468       477       486
CAC TAC ACG GGA CAC CAG GAC GTG GTA TTA GAT CAT GCG TAT CAC GGC CAC
 H   Y   T   G   H   Q   D   V   V   L   D   H   A   Y   H   G   H 495       504       513       522       531       540
CTG AGC TCC CTG ATT GAC ATC AGT CCC TAC AAG TTC CGC AAC CTG GAT GGC CAG
 L   S   S   L   I   D   I   S   P   Y   K   F   R   N   L   D   G   Q 549       558       567       576       585       594
AAG GAG TGG GTC CAC GTG GCA CCT CTC CCA GAC ACC TAC CGG GGC CCC TAC CGG
 K   E   W   V   H   V   A   P   L   P   D   T   Y   R   G   P   Y   R 603       612       621       630       639       648
GAG GAC CAC CCC AAC CCA GCT ATG GCC TAT GCC AAC GAG GTG AAA CGT GTG GTC
 E   D   H   P   N   P   A   M   A   Y   A   N   E   V   K   R   V   V 657       666       675       684       693       702
AGC AGT GCA CAG GAG AAG GGC AGG AAG ATT GCA GCC TTC TTC GCT GAG TCT CTG
 S   S   A   Q   E   K   G   R   K   I   A   A   F   F   A   E   S   L
```

Figure 1B

```
CCC AGT GTG GGA GGG CAG ATC ATT CCC CCT GCT GGC TAC TTC TCC CAA GTG GCA
 P   S   V   G   G   Q   I   I   P   P   A   G   Y   F   S   Q   V   A
711         720             729             738             747         756

GAG CAC ATC CGC AAG GCC GGA GGG GTC TTT GTT GCA GAT GAG ATC CAG GTT GGC
 E   H   I   R   K   A   G   G   V   F   V   A   D   E   I   Q   V   G
765         774             783             792             801         810

TTT GGC CGG GTA GGC AAG CAC TTC TGG GCC TTC CAG CTC CAG GGA AAA GAC TTC
 F   G   R   V   G   K   H   F   W   A   F   Q   L   Q   G   K   D   F
819         828             837             846             855         864

GTC CCT GAC ATC GTC ACC ATG GGC AAG TCC ATT GGC AAC GGC CAC CCT GTT GCC
 V   P   D   I   V   T   M   G   K   S   I   G   N   G   H   P   V   A
873         882             891             900             909         918

TGC GTG GCC GCA ACC CAG CCT GTG GCG AGG GCA TTT GAA GCC ACC GGC GTT GAG
 C   V   A   A   T   Q   P   V   A   R   A   F   E   A   T   G   V   E
927         936             945             954             963         972

TAC TTC AAC ACG TTT GGG GGC AGC CCA GTG TCC TGC GCT GTG GGG CTG GCC GTC
 Y   F   N   T   F   G   G   S   P   V   S   C   A   V   G   L   A   V
981         990             999             1008            1017        1026
```

Figure 1C

```
      1035            1044            1053            1062            1071            1080
CTG AAT GTC TTG GAG AAG GAG CAG CTC CAG GAT CAT GCC ACC AGT GTA GGC AGC
 L   N   V   L   E   K   E   Q   L   Q   D   H   A   T   S   V   G   S 1089            1098            1107            1116            1125            1134
TTC CTG ATG CAG CTC CTC GGG CAG CAA AAA ATC AAA CAT CCC ATC GTC GGG GAT
 F   L   M   Q   L   L   G   Q   Q   K   I   K   H   P   I   V   G   D 1143            1152            1161            1170            1179            1188
GTC AGG GGT GTT GGG CTC TTC ATT GGT GTG GAT CTG ATC AAA GAT GAG GCC ACA
 V   R   G   V   G   L   F   I   G   V   D   L   I   K   D   E   A   T 1197            1206            1215            1224            1233            1242
AGG ACA CCA GCA ACT GAA GAG GCT GCC TAC TTG GTA TCA AGG CTG AAG GAG AAC
 R   T   P   A   T   E   E   A   A   Y   L   V   S   R   L   K   E   N 1251            1260            1269            1278            1287            1296
TAC GTT TTG CTG AGC ACT GAT GGC CCT GGG AGG AAC ATC CTG AAG TTT AAG CCC
 Y   V   L   L   S   T   D   G   P   G   R   N   I   L   K   F   K   P 1305            1314            1323            1332            1341            1350
CCA ATG TGC TTC AGC CTG GAC AAT GCA CGG CAG GTG GCA AAG CTG GAT GCC
 P   M   C   F   S   L   D   N   A   R   Q   V   A   K   L   D   A
```

Figure 1D

```
            1359           1368           1377           1386           1395           1404
ATT CTG ACT GAC ATG GAA GAG AAG GTG AGA AGT TGT GAA ACG CTG AGG CTC CAG
 I   L   T   D   M   E   E   K   V   R   S   C   E   T   L   R   L   Q
            1413           1422           1431           1440           1449           1458
CCC TAA GCC AGC CCT GCT CTG CCT AAG TGT ACT CCA GAA GAA ACT CAT CTC ATC
 P   *
            1467           1476           1485           1494           1503           1512
CAA ATA CAC GCT ATT GAG AAG GCG AGC CTG ACC TCC CTC TTA CAG ATA AAG TCA
            1521           1530           1539           1548           1557           1566
GCT TTC AGA GGC TCA GGG TGG GGG CTG CCC GAG GCC ATA ATG CTA CCC ACC
            1575           1584           1593           1602           1611           1620
CCC TCC TCC TAA CCA CTG GTC TGT TGG AAT AAC CCA GAT GTC TGC ATC CCC TCA
            1629           1638           1647           1656           1665           1674
AGT CAG TCA ATT TCC TTT CTG TCC ACT GGG GGT GGA ATG GGG TAG GGT GGG ATA
            1683           1692           1701           1710           1719           1728
CTT TAA AGT GCT CCT TAA ATA AAT TAG ACC AGA CCA GTG TAT TTC TAA AGA
            1737           1746           1755           1764           1773           1782
AAA TCC TGA CAT GCA CAC CCA TTA AAA ATA GTA CAT TTT ACA GTG AAA AAA AAA

AAA A 3'
```

Figure 1E

```
1    MAADQRPKADTLALRQRL----------ISSSCRLFFP--------- 3128715
1    MSLAWRTLQKAFYLETSLRILQMRPSLSCASRIYVVPKLTL       GI 1944136

29   ---------------------------------------------- 3128715
41   HTKHNMPPCDFSPEKYQSLAYNHVLEIHKQHLSPVNTAYF------- GI 1944136

29   EDPVKIVRAQGQYMYDEQGAEYIDCISNVAHVG--HCHPL------- 3128715
81   QKPLLLHQGHMEWLFDSEGNRYLDFFSGIVTVGVGHCHPK        GI 1944136

67   VVQAAHEQNQVL-NTNSRYLHDNIVDYAQRLSETLPEQLC        3128715
121  VTAVAKKQMDRLWHTSSVFFHSPMHEYAERLSALLPEPLK        GI 1944136

106  VFYFLNSGSEANDLALRLARHYTGHQDVVVLDHAYHGHLS        3128715
161  VIFLVNSGSEANDLAMVMARAYSNHTDIISFRGAYHGCSP        GI 1944136

146  ---SLIDISPYKFRNLDGQKEWVHVAPLPDTYRGPYREDH        3128715
201  YTLGLTNVGIYKMKVPSTIA--CQSTMCPDVFRGPWGGSH        GI 1944136

183  -PNPAMAYANEVKRVVSSAQEKGR---------------K        3128715
239  CRDSPVQTVRKCSCAPDGCQAKERYIEQFKDTLNTSVATS        GI 1944136
```

HUMAN BETA-ALANINE-PYRUVATE AMINOTRANSFERASE

This application is a divisional application of U.S. application Ser. No. 09/015,296, filed Jan. 29, 1998 now U.S. Pat. No. 6,103,471, all of which application and patents are hereby incorporated herein by reference.

FIELD OF THE INVENTION

This invention relates to nucleic acid and amino acid sequences of a human beta-alanine-pyruvate aminotransferase and to the use of these sequences in the diagnosis, treatment, and prevention of diseases associated with immune disorders and cancer.

BACKGROUND OF THE INVENTION

Aminotransferases catalyze the transfer of an alpha-amino group from an alpha-amino acid to an alpha-keto acid. These enzymes, also called transaminases, generally funnel alpha-amino groups from a variety of amino acids to alpha-ketoglutarate for conversion into $NH_4^+$. Aspartate aminotransferase, one of the most important of these enzymes, catalyzes the transfer of the amino group of aspartate to alpha-ketoglutarate. In most vertebrates, $NH_4^+$ is converted into urea, and is excreted.

In terrestrial vertebrates, urea is synthesized by the urea cycle. One of the nitrogen atoms of the urea synthesized by this pathway is transferred from the amino acid aspartate. The other nitrogen atom and the carbon atom are derived from $NH_4^+$ and $CO_2$. Ornithine is the carrier of these carbon and nitrogen atoms. Other reactions of the urea cycle lead to the synthesis of arginine from ornithine, an amino acid that occurs naturally as an intermediate in arginine biosynthesis. Alanine aminotransferase, which is also prevalent in mammalian tissue, catalyzes the transfer of the amino group of alanine to alpha-ketoglutarate which producing pyruvate and glutamate. Glutamate is then oxadatively deaminated, yielding $NH_4^+$ and regenerating alpha-ketoglutarate. (See, e.g., Stryer, L., 1988 (3rd ed.). Freeman.) High levels of $NH_4^+$ are toxic to humans. The synthesis of urea in the liver is the major route of removal of $NH_4^+$, and a complete block of any of the steps of the urea cycle is usually fatal, because there is no known alternative pathway for the synthesis of urea. Inherited disorders caused by a partial block of each of the urea cycle reactions have been diagnosed. The most common condition is an elevated level of $NH_4^+$ in the blood (hyperammonemia). A nearly total deficiency of any of the urea cycle enzymes results in coma or death shortly after birth.

The discovery of a new human beta-alanine-pyruvate aminotransferase and the polynucleotides encoding it satisfies a need in the art by providing new compositions which are useful in the diagnosis, treatment, and prevention of diseases associated with immune disorders and cancer.

SUMMARY OF THE INVENTION

The invention features a substantially purified polypeptide, human beta-alanine-pyruvate aminotransferase (HAPA), comprising a sequence of SEQ ID NO:1 or a fragment of SEQ ID NO:1.

The invention further provides a substantially purified variant of HAPA having at least 90% amino acid identity to the sequence of SEQ ID NO:1 or a fragment of SEQ ID NO:1. The invention also provides an isolated and purified polynucleotide encoding the polypeptide comprising the sequence of SEQ ID NO:1 or a fragment of SEQ ID NO:1. The invention also includes an isolated and purified polynucleotide variant having at least 90% polynucleotide identity to the polynucleotide encoding the polypeptide comprising the sequence of SEQ ID NO:1 or a fragment of SEQ ID NO:1.

Additionally, the invention provides a composition comprising a polynucleotide encoding the polypeptide comprising the sequence of SEQ ID NO:1 or a fragment of SEQ ID NO:1. The invention further provides an isolated and purified polynucleotide which hybridizes under stringent conditions to the polynucleotide encoding the polypeptide comprising the sequence of SEQ ID NO:1 or a fragment of SEQ ID NO:1, as well as an isolated and purified polynucleotide which is complementary to the polynucleotide encoding the polypeptide comprising the sequence of SEQ ID NO:1 or a fragment of SEQ ID NO:1.

The invention also provides an isolated and purified polynucleotide comprising a sequence of SEQ ID NO:2 or a fragment of SEQ ID NO:2, and an isolated and purified polynucleotide variant having at least 90% polynucleotide identity to the polynucleotide comprising the sequence of SEQ ID NO:2 or a fragment of SEQ ID NO:2. The invention also provides an isolated and purified polynucleotide which is complementary to the polynucleotide comprising the sequence of SEQ ID NO:2 or a fragment of SEQ ID NO:2.

The invention further provides an expression vector containing at least a fragment of the polynucleotide encoding the polypeptide comprising the sequence of SEQ ID NO:1 or a fragment of SEQ ID NO:1. In another aspect, the expression vector is contained within a host cell.

The invention also provides a method for producing a polypeptide comprising a sequence of SEQ ID NO:1 or a fragment of SEQ ID NO:1, the method comprising the steps of: (a) culturing the host cell containing an expression vector containing at least a fragment of a polynucleotide encoding HAPA under conditions suitable for the expression of the polypeptide; and (b) recovering the polypeptide from the host cell culture.

The invention also provides a pharmaceutical composition comprising a substantially purified HAPA having the sequence of SEQ ID NO:1 or a fragment of SEQ ID NO:1 in conjunction with a suitable pharmaceutical carrier.

The invention further includes a purified antibody which binds to a polypeptide comprising the sequence of SEQ ID NO:1 or a fragment of SEQ ID NO:1, as well as a purified agonist and a purified antagonist of the polypeptide.

The invention also provides a method for treating or preventing a cancer, the method comprising administering to a subject in need of such treatment an effective amount of an antagonist to HAPA.

The invention also provides a method for treating or preventing an immune response, the method comprising administering to a subject in need of such treatment an effective amount of an antagonist to HAPA.

The invention also provides a method for detecting a polynucleotide encoding HAPA in a biological sample containing nucleic acids, the method comprising the steps of: (a) hybridizing the complement of the polynucleotide encoding the polypeptide comprising the sequence of SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding HAPA in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of HAPA. The alignment was produced using MACDNASIS PRO software (Hitachi Software Engineering Co. Ltd., S. San Francisco, Calif.).

FIGS. 2A and 2B show the amino acid sequence alignments among HAPA (3128715; SEQ ID NO:1) and beta-alanine-pyruvate aminotransferase from rat (GI 1944136; SEQ ID NO:3), produced using the multisequence alignment program of LASERGENE software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"HAPA," as used herein, refers to the amino acid sequences of substantially purified HAPA obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HAPA, increases or prolongs the duration of the effect of HAPA. Agonists may include proteins, nucleic acids, carbohydrates, or any other molecules which bind to and modulate the effect of HAPA.

An "allele" or an "allelic sequence," as these terms are used herein, is an alternative form of the gene encoding HAPA. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HAPA, as described herein, include those sequences with deletions, insertions, or substitutions of different nucleotides, resulting in a polynucleotide the same HAPA or a polypeptide with at least one functional characteristic of HAPA. Included within this definition are polymorphisms which may or may not be readily detectable using a particular oligonucleotide probe of the polynucleotide encoding HAPA, and improper or unexpected hybridization to alleles, with a locus other than the normal chromosomal locus for the polynucleotide sequence encoding HAPA. The encoded protein may also be "altered," and may contain deletions, insertions, or substitutions of amino acid residues which produce a silent change and result in a functionally equivalent HAPA. Deliberate amino acid substitutions may be made on the basis of similarity in polarity, charge, solubility, hydrophobicity, hydrophilicity, and/or the amphipathic nature of the residues, as long as the biological or immunological activity of HAPA is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of HAPA which are preferably about 5 to about 15 amino acids in length and which retain some biological activity or immunological activity of HAPA. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp. 1–5.)

The term "antagonist," as it is used herein, refers to a molecule which, when bound to HAPA, decreases the amount or the duration of the effect of the biological or immunological activity of HAPA. Antagonists may include proteins, nucleic acids, carbohydrates, antibodies, or any other molecules which decrease the effect of HAPA.

As used herein, the term "antibody" refers to intact molecules as well as to fragments thereof, such as Fab, F(ab')$_2$, and Fv fragments, which are capable of binding the epitopic determinant. Antibodies that bind HAPA polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HAPA, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding HAPA or fragments of HAPA may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR (PE Biosystems, Foster City, Calif.) in the 5' and/or the 3' direction, and resequenced, or which has been assembled from the overlapping sequences of more than one Incyte Clone using a computer program for fragment assembly, such as the GELVIEW Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding HAPA, by northern analysis is indicative of the presence of nucleic acids encoding HAPA in a sample, and thereby correlates with expression of the transcript from the polynucleotide encoding HAPA.

A "deletion," as the term is used herein, refers to a change in the amino acid or nucleotide sequence that results in the absence of one or more amino acid residues or nucleotides.

The term "derivative," as used herein, refers to the chemical modification of HAPA, of a polynucleotide sequence encoding HAPA, or of a polynucleotide sequence complementary to a polynucleotide sequence encoding HAPA. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (LASERGENE software package, DNASTAR, Inc., Madison Wis.). The MEGALIGN program can create alignments between two or more sequences according to different methods, e.g., the Clustal Method. (Higgins, D. G. and P. M. Sharp (1988) Gene 73:237–244.) The Clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be calculated by the Clustal Method, or by other methods known in the art, such as the Jotun Hein Method. (See, e.g., Hein, J. (1990) Methods in Enzymology 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an array of distinct polynucleotides or oligonucleotides arrayed on a substrate, such as paper, nylon or any other type of membrane, filter, chip, glass slide, or any other suitable solid support.

The term "modulate," as it appears herein, refers to a change in the activity of HAPA. For example, modulation may cause an increase or a decrease in protein activity, binding characteristics, or any other biological, functional, or immunological properties of HAPA.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in reading frame, certain genetic elements, e.g., repressor genes, are not contiguously linked to the encoded polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimers," "primers," "oligomers," and "probes," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding HAPA, or fragments thereof, or HAPA itself may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 µg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, and refers to cells which transiently express the inserted DNA or RNA for limited periods of time.

A "variant" of HAPA, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software.

THE INVENTION

The invention is based on the discovery of a new human beta-alanine-pyruvate aminotransferase (HAPA), the polynucleotides encoding HAPA, and the use of these compositions for the diagnosis, treatment, or prevention of diseases associated with immune disorders and cancer.

Nucleic acids encoding the HAPA of the present invention were first identified in Incyte Clone 3128715 from the lung tumor cDNA library (LUNGTUT12) using a computer search for amino acid sequence alignments. A consensus sequence, SEQ ID NO:2, was derived from the following overlapping and/or extended nucleic acid sequences: Incyte Clones 3128715 (LUNGTUT12), 3234316 (COLNUCT03), 2075940 (ISLTNOT01), 3186992 (THYMNON04), 077724 (SYNORAB01), 1252424 (LUNGFET03), and 1620917 (BRAITUT13).

In one embodiment, the invention encompasses a polypeptide comprising the amino acid sequence of SEQ ID NO:1, as shown in FIGS. 1A, 1B, 1C, 1D, and 1E. HAPA is 450 amino acids in length and has six potential casein kinase II phosphorylation sites at residues $T_{99}$, $S_{112}$, $S_{146}$, $S_{199}$, $T_{302}$, and $T_{434}$; three potential protein kinase C phosphorylation sites at residues $S_{22}$, $T_{173}$, and $T_{445}$; and one potential aminotransferase class-III pyridoxal-phosphate attachment site between residue $F_{243}$ and $G_{283}$, in which $K_{278}$ is the pyridoxal-phosphate attachment site. As shown in FIGS. 2A and 2B, HAPA has chemical and structural homology with beta-alanine-pyruvate aminotransferase (GI 1944136; SEQ ID NO:3). In particular, HAPA and beta-alanine-pyruvate aminotransferase from rat share 35% identity and the active lysine attachment site at residue $K_{278}$ in the pyridoxal-phosphate attachment site. Fragments of the nucleic acid sequence (SEQ ID NO:2) useful for hybridization experiments are from about $C_{97}$ to about $G_{108}$ and about $A_{220}$ to about $G_{235}$. Northern analysis shows the expression of this sequence in various libraries, at least 37% of which are immortalized or cancerous and at least 28% of which involve immune response.

The invention also encompasses HAPA variants. A preferred HAPA variant is one which has at least about 80%, more preferably at least about 90%, and most preferably at least about 95% amino acid sequence identity to the HAPA amino acid sequence, and which contains at least one functional or structural characteristic of HAPA.

The invention also encompasses polynucleotides which encode HAPA. In a particular embodiment, the invention encompasses a polynucleotide sequence comprising the sequence of SEQ ID NO:2, which encodes an HAPA.

The invention also encompasses a variant of a polynucleotide sequence encoding HAPA. In particular, such a variant polynucleotide sequence will have at least about 80%, more preferably at least about 90%, and most preferably at least about 95% polynucleotide sequence identity to the polynucleotide sequence encoding HAPA. A particular aspect of the invention encompasses a variant of SEQ ID NO:2 which has at least about 80%, more preferably at least about 90%, and most preferably at least about 95% polynucleotide sequence identity to SEQ ID NO:2. Any one of the polynucleotide variants described above can encode an amino acid sequence which contains at least one functional or structural characteristic of HAPA.

It will be appreciated by those skilled in the art that as a result of the degeneracy of the genetic code, a multitude of polynucleotide sequences encoding HAPA, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HAPA, and all such variations are to be considered as being specifically disclosed.

Although nucleotide sequences which encode HAPA and its variants are preferably capable of hybridizing to the nucleotide sequence of the naturally occurring HAPA under appropriately selected conditions of stringency, it may be advantageous to produce nucleotide sequences encoding HAPA or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HAPA and its derivatives without altering the encoded amino acid sequences include the production of RNA transcripts having more desirable properties, such as a greater half-life, than transcripts produced from the naturally occurring sequence.

The invention also encompasses production of DNA sequences which encode HAPA and HAPA derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HAPA or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency. (See, e.g., Wahl, G. M. and S. L. Berger (1987) Methods Enzymol. 152:399–407; and Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, SEQUENASE (US Biochemical Corp., Cleveland, Ohio), Taq DNA polymerase, thermostable T7 polymerase (Amersham, Chicago, Ill.), or combinations of polymerases and proofreading exonucleases such as those found in the ELONGASE Amplification System (GIBCO/BRL, Gaithersburg, Md.). Preferably, the process is automated with machines such as the MICROLAB 2200 (Hamilton, Reno, Nev.), DNA ENGINE thermal cycler (PTC200; MJ Research, Watertown, Mass.) and the ABI PRISM sequencing systems (PE Biosystems).

The nucleic acid sequences encoding HAPA may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (See, e.g., Sarkar, G. (1993) PCR Methods Applic. 2:318–322.) In particular, genomic DNA is first amplified in the presence of a primer complementary to a linker sequence within the vector and a primer specific to the region predicted to encode the gene. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (See, e.g., Triglia, T. et al. (1988) Nucleic Acids Res. 16:8186.) The primers may be designed using commercially available software such as OLIGO 4.06 Primer Analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (See, e.g., Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker, J. D. et al. (1991) Nucleic Acids Res. 19:3055–3060.) Additionally, one may use PCR, nested primers, and PROMOTERFINDER libraries (Clontech, Palo Alto, Calif.) to walk genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., GENOTYPER and SEQUENCE NAVIGATOR, PE Biosystetms), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HAPA may be used in recombinant DNA molecules to direct expression of HAPA, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HAPA.

As will be understood by those of skill in the art, it may be advantageous to produce HAPA-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HAPA-encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HAPA may be ligated to a heterologous sequence to encode a fusion protein. For example, to screen peptide libraries for inhibitors of HAPA activity, it may be useful to encode a chimeric HAPA protein that can be recognized by a commercially available antibody. A fusion protein may also be engineered to contain a cleavage site located between the HAPA encoding sequence and the heterologous protein sequence, so that HAPA may be cleaved and purified away from the heterologous moiety.

In another embodiment, sequences encoding HAPA may be synthesized, in whole or in part, using chemical methods well known in the art. (See, e.g., Caruthers, M. H. et al. (1980) Nucl. Acids Symp. Ser. (7):215–223, and Horn, T. et al. (1980) Nucl. Acids Symp. Ser. (7):225–232.) Alternatively, the protein itself may be produced using chemical methods to synthesize the amino acid sequence of HAPA, or a fragment thereof. For example, peptide synthesis can be performed using various solid-phase techniques. (See, e.g., Roberge, J. Y. et al. (1995) Science 269:202–204.) Automated synthesis may be achieved using the ABI 431A Peptide synthesizer (PE Biosystems).

The newly synthesized peptide may be substantially purified by preparative high performance liquid chromatography. (See, e.g., Chiez, R. M. and F. Z. Regnier (1990) Methods Enzymol. 182:392–421.) The composition of the synthetic peptides may be confirmed by amino acid analysis or by sequencing. (See, e.g., Creighton, T. (1983) *Proteins Structures and Molecular Properties*, WH Freeman and Co., New York, N.Y.) Additionally, the amino acid sequence of HAPA, or any part thereof, may be altered during direct synthesis and/or combined with sequences from other proteins, or any part thereof, to produce a variant polypeptide.

In order to express a biologically active HAPA, the nucleotide sequences encoding HAPA or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding HAPA and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding HAPA. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions, e.g., enhancers, promoters, and 5' and 3' untranslated regions, of the vector and polynucleotide sequences encoding HAPA which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters, e.g., hybrid lacZ promoter of the BLUESCRIPT phagemid (Stratagene, La Jolla, Calif.) or PSPORT1 plasmid (GIBCO/BRL), may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HAPA, vectors based on SV40 or EBV may be used with an appropriate selectable marker.

In bacterial systems, a number of expression vectors may be selected depending upon the use intended for HAPA. For example, when large quantities of HAPA are needed for the induction of antibodies, vectors which direct high level expression of fusion proteins that are readily purified may be used. Such vectors include, but are not limited to, multifunctional *E. coli* cloning and expression vectors such as BLUESCRIPT (Stratagene), in which the sequence encoding HAPA may be ligated into the vector in frame with sequences for the amino-terminal Met and the subsequent 7 residues of β-galactosidase so that a hybrid protein is produced, and pIN vectors. (See, e.g., Van Heeke, G. and S. M. Schuster (1989) J. Biol. Chem. 264:5503–5509.) pGEX vectors (Pharmacia Biotech, Uppsala, Sweden) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. (See, e.g., Ausubel, supra; and Grant et al. (1987) Methods Enzymol. 153:516–544.)

In cases where plant expression vectors are used, the expression of sequences encoding HAPA may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, e.g., Hobbs, S. or Murry, L. E. in *McGraw Hill Yearbook of Science and Technology* (1992) McGraw Hill, New York, N.Y.; pp. 191–196.)

An insect system may also be used to express HAPA. For example, in one such system, *Autographa californica* nuclear polyhedrosis virus (AcNPV) is used as a vector to express foreign genes in *Spodoptera frugiperda* cells or in Trichoplusia larvae. The sequences encoding HAPA may be cloned into a non-essential region of the virus, such as the polyhedrin gene, and placed under control of the polyhedrin promoter. Successful insertion of sequences encoding HAPA will render the polyhedrin gene inactive and produce recombinant virus lacking coat protein. The recombinant viruses may then be used to infect, for example, *S. frugiperda* cells or Trichoplusia larvae in which HAPA may be expressed. (See, e.g., Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding HAPA may be ligated into an adenovirus transcription/translation complex consisting of the late promoter and tripartite leader sequence. Insertion in a non-essential E1 or E3 region of the viral genome may be used to obtain a viable virus which is capable of expressing HAPA in infected host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding HAPA. Such signals include the ATG initiation codon and adjacent sequences. In cases where sequences encoding HAPA and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing HAPA can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in tk$^-$ or apr$^-$ cells, respectively. (See, e.g., Wigler, M. et al. (1977) Cell 11:223–232; and Lowy, I. et al. (1980) Cell 22:817–823) Also, antimetabolite, antibiotic, or herbicide resistance can be used as the basis for selection. For example, dhfr confers resistance to methotrexate; npt confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB, which allows cells to utilize indole in place of tryptophan, or hisD, which allows cells to utilize histinol in place of histidine. (See, e.g., Hartman, S. C. and R. C. Mulligan (1988) Proc. Natl. Acad. Sci. 85:8047–8051.) Recently, the use of visible markers has gained popularity with such markers as anthocyanins, β glucuronidase and its substrate GUS, luciferase and its substrate luciferin. Green fluorescent proteins (GFP) (Clontech, Palo Alto, Calif.) are also used (See, e.g., Chalfie, M. et al. (1994) Science 263:802–805.) These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding HAPA is inserted within a marker gene sequence, transformed cells containing sequences encoding HAPA can be identified by the absence of marker gene function. Alternatively, a marker gene can be placed in tandem with a sequence encoding HAPA under the control of a single promoter. Expression of the marker gene in response to induction or selection usually indicates expression of the tandem gene as well.

Alternatively, host cells which contain the nucleic acid sequence encoding HAPA and express HAPA may be identified by a variety of procedures known to those of skill in the art. These procedures include, but are not limited to, DNA-DNA or DNA-RNA hybridizations and protein bio-assay or immunoassay techniques which include membrane, solution, or chip based technologies for the detection and/or quantification of nucleic acid or protein sequences.

The presence of polynucleotide sequences encoding HAPA can be detected by DNA-DNA or DNA-RNA hybridization or amplification using probes or fragments or fragments of polynucleotides encoding HAPA. Nucleic acid amplification based assays involve the use of oligonucleotides or oligomers based on the sequences encoding HAPA to detect transformants containing DNA or RNA encoding HAPA.

A variety of protocols for detecting and measuring the expression of HAPA, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HAPA is preferred, but a competitive binding assay may be employed. These and other assays are well described in the art. (See, e.g., Hampton, R. et al. (1990) *Serological Methods, a Laboratory Manual*, APS Press, St Paul, Minn., Section IV; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HAPA include oligolabeling, nick translation, end-labeling, or PCR amplification using a labeled nucleotide. Alternatively, the sequences encoding HAPA, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech (Piscataway N.J.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HAPA may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HAPA may be designed to contain signal sequences which direct secretion of HAPA through a prokaryotic or eukaryotic cell membrane. Other constructions may be used to join sequences encoding HAPA to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the HAPA encoding sequence may be used to facilitate purification. One such expression vector provides for expression of a fusion protein containing HAPA and a nucleic acid encoding 6 histidine residues preceding a thioredoxin or an enterokinase cleavage site. The histidine residues facilitate purification on immobilized metal ion affinity chromatography. (IMIAC) (See, e.g., Porath, J. et al. (1992) Prot. Exp. Purif. 3: 263–281.) The enterokinase cleavage site provides a means for purifying HAPA from the fusion protein. (See, e.g., Kroll, D. J. et al. (1993) DNA Cell Biol. 12:441453.)

Fragments of HAPA may be produced not only by recombinant production, but also by direct peptide synthesis using solid-phase techniques. (See, e.g., Creighton, T. E. (1984) Protein: Structures and Molecular Properties, pp. 55–60, W.H. Freeman and Co., New York, N.Y.) Protein synthesis may be performed by manual techniques or by automation. Automated synthesis may be achieved, for example, using the ABI 431A Peptide synthesizer (PE Biosystems). Various fragments of HAPA may be synthesized separately and then combined to produce the full length molecule.

Therapeutics

Chemical and structural homology exists between HAPA and beta-alanine-pyruvate aminotransferase from rat (GI1944136). In addition, HAPA is expressed in tissues associated with immune disorders and cancer. Therefore, HAPA appears to play a role in immune disorders and cancer.

Therefore, in one embodiment, an antagonist of HAPA or a fragment or derivative thereof may be administered to a subject to treat or prevent a cancer. Such cancers may include, but are not limited to, adenocarcinoma, leukemia, lymphoma, melanoma, myeloma, sarcoma, and teratocarcinoma; and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HMAP may be used directly as an antagonist or indirectly as a targeting or delivery mechanism for bringing a pharmaceutical agent to cells or tissues which express HMAP.

In another embodiment, a vector expressing the complement of the polynucleotide encoding HMAP may be administered to a subject to treat or prevent a cancer including, but not limited to, those described above.

Therefore, in another embodiment, an antagonist of HMAP may be administered to a subject to prevent or treat an immune disorder. Immune disorders may include, but are not limited to AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma. In one aspect, an antibody which specifically binds HMAP may be used directly as an antagonist or indirectly as a targeting or delivery mechanism for bringing a pharmaceutical agent to cells or tissues which express HMAP.

In another embodiment, a vector expressing the complement of the polynucleotide encoding HMAP may be administered to a subject to treat or prevent an immune disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HAPA may be produced using methods which are generally known in the art. In particular, purified HAPA may be used to produce antibodies or to screen libraries of pharmaceutical agents to identify those which specifically bind HAPA. Antibodies to HAPA may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HAPA or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HAPA have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HAPA amino acids may be fused with those of another protein, such as KLH, and antibodies to the chimeric molecule may be produced.

Monoclonal antibodies to HAPA may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HAPA-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for HAPA may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HAPA and its specific antibody. A two-site, monoclonal-based immunoassay utilizing monoclonal antibodies reactive to two non-interfering HAPA epitopes is preferred, but a competitive binding assay may also be employed. (Maddox, supra.)

In another embodiment of the invention, the polynucleotides encoding HAPA, or any fragment or complement thereof, may be used for therapeutic purposes. In one aspect, the complement of the polynucleotide encoding HAPA may be used in situations in which it would be desirable to block the transcription of the mRNA. In particular, cells may be transformed with sequences complementary to polynucleotides encoding HAPA. Thus, complementary molecules or fragments may be used to modulate HAPA activity, or to achieve regulation of gene function. Such technology is now well known in the art, and sense or antisense oligonucleotides or larger fragments can be designed from various locations along the coding or control regions of sequences encoding HAPA.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding HAPA. (See, e.g., Sambrook, supra; and Ausubel, supra.) Genes encoding HAPA can be turned off by transforming a cell or tissue with expression vectors which express high levels of a polynucleotide, or fragment thereof, encoding HAPA. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HAPA. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HAPA.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HAPA. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HAPA, antibodies to HAPA, and mimetics, agonists, antagonists, or inhibitors of HAPA. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HAPA, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HAPA or fragments thereof, antibodies of HAPA, and agonists, antagonists or inhibitors of HAPA, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of toxic to therapeutic effects is the therapeutic index, and it can be expressed as the LD50/ED50 ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HAPA may be used for the diagnosis of disorders characterized by expression of HAPA, or in assays to monitor patients being treated with HAPA or agonists, antagonists, or inhibitors of HAPA. Antibodies useful for diagnostic purposes may be prepared in the same manner as described above for therapeutics. Diagnostic assays for HAPA include methods which utilize the antibody and a label to detect HAPA in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HAPA, including ELISAs, RIAs, and FACS, are known in the art and provide a basis for diagnosing altered or abnormal levels of HAPA expression. Normal or standard values for HAPA expression are established by combining body fluids or cell extracts taken from normal mammalian subjects, preferably human, with antibody to HAPA under conditions suitable for complex formation. The amount of standard complex formation may be quantitated by various methods, preferably by photometric means. Quantities of HAPA expressed in subject samples, control and disease, from biopsied tissues are compared with the standard values. Deviation between standard and subject values establishes the parameters for diagnosing disease.

In another embodiment of the invention, the polynucleotides encoding HAPA may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HAPA may be correlated with disease. The diagnostic assay may be used to determine absence, presence, and excess expression of HAPA, and to monitor regulation of HAPA levels during therapeutic intervention.

In one aspect, hybridization with PCR probes which are capable of detecting polynucleotide sequences, including genomic sequences, encoding HAPA or closely related molecules may be used to identify nucleic acid sequences which encode HAPA. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HAPA, alleles, or related sequences.

Probes may also be used for the detection of related sequences, and should preferably contain at least 50% of the nucleotides from any of the HAPA encoding sequences. The hybridization probes of the subject invention may be DNA or RNA and may be derived from the sequence of SEQ ID NO:2 or from genomic sequences including promoters, enhancers, and introns of the HAPA gene.

Means for producing specific hybridization probes for DNAs encoding HAPA include the cloning of polynucleotide sequences encoding HAPA or HAPA derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding HAPA may be used for the diagnosis of a disorder associated with expression of HAPA. Examples of such a disorder include, but are not limited to, cancers such as adenocarcinoma, leukemia, lymphoma, melanoma, myeloma, sarcoma, and teratocarcinoma; and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immune disorders such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma. The polynucleotide sequences encoding HAPA may be used in Southern or northern analysis, dot blot, or other membrane-based technologies; in PCR technologies; or in dipstick, pin, ELISA assays or microarrays utilizing fluids or tissues from patient biopsies to detect altered HAPA expression. Such qualitative or quantitative methods are well known in the art. The polynucleotide sequences encoding HAPA may be used in Southern or northern analysis, dot blot, or other membrane-based technologies; in PCR technologies; in dipstick, pin, and ELISA assays; and in microarrays utilizing fluids or tissues from patients to detect altered HAPA expression. Such qualitative or quantitative methods are well known in the art.

In a particular aspect, the nucleotide sequences encoding HAPA may be useful in assays that detect the presence of associated disorders, particularly those mentioned above. The nucleotide sequences encoding HAPA may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HAPA in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HAPA, a normal or standard profile for expression is established. This may be accomplished by combining body fluids or cell extracts taken from normal subjects, either animal or human, with a sequence, or a fragment thereof, encoding HAPA, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HAPA may involve the use of PCR. These oligomers may be chemically synthesized, generated enzymatically, or produced in vitro. Oligomers will preferably contain a fragment of a polynucleotide encoding HAPA, or a fragment of a polynucleotide complementary to the polynucleotide encoding HAPA, and will be employed under optimized conditions for identification of a specific gene or condition. Oligomers may also be employed under less stringent conditions for detection or quantitation of closely related DNA or RNA sequences.

Methods which may also be used to quantitate the expression of HAPA include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al.

(1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding HAPA may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding HAPA on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, HAPA, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HAPA and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with HAPA, or fragments thereof, and washed. Bound HAPA is then detected by methods well known in the art. Purified HAPA can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HAPA specifically compete with a test compound for binding HAPA. In this manner, antibodies can be used to detect the presence of any peptide which shares one or more antigenic determinants with HAPA.

In additional embodiments, the nucleotide sequences which encode HAPA may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. LUNGTUT12 cDNA Library Construction

The LUNGTUT12 cDNA library was constructed from cancerous lung tissue obtained from a 70-year-old Caucasian female,(specimen #0319A) during a lung lobectomy. Pathology for the left upper lobe lung tissue indicated grade 3 (of 4) adenocarcinoma, forming a mass which abuts but does not involve the pleura. Vascular invasion was present. The lobectomy specimen contained no residual carcinoma. The bronchial margin was free of involvement. Multiple (9) intrapulmonary peribronchial lymph nodes were negative for tumor. Pathology for the left lower lobe lung tissue indicated lung parenchyma with focal subpleural fibrosis. Multiple superior mediastinal (2 left tracheo-bronchial), inferior mediastinal (8 subcarinal; 4 inferior pulmonary ligament), 6 left lower lobe bronchus, and 4 left fissure lymph nodes were negative for tumor. Patient history included tobacco abuse, depressive disorder, anxiety state, deviated nasal septum, malignant skin neoplasm, and a cesarean delivery. Previous surgeries included an appendectomy. Family history included benign hypertension, cerebrovascular disease, and renal failure in the father; congestive heart failure, malignant colon neoplasm, and depressive disorder in the mother; and primary malignant liver neoplasm in a sibling.

The frozen tissues was homogenized and lysed in TRIZOL reagent (1 gm tissue/10 ml Trizol; Cat. #10296-028; GIBCO/BRL), a monoplastic solution of phenol and guanidine isothiocyanate, using a POLYTRON homogenizer (PT-3000; Brinkmann Instruments, Westbury, N.Y.). After a brief incubation on ice, chloroform was added (1:5 v/v) and the lysate was centrifuged. The upper chloroform layer was removed to a fresh tube and the RNA extracted with isopropanol, resuspended in DEPC-treated water, and treated with DNase for 25 min at 37° C. RNA extraction and precipitation were repeated as before. The mRNA was then isolated using the OLIGOTEX kit (QIAGEN, Chatsworth, Calif.) and used to construct the cDNA library.

II Isolation and Sequencing of cDNA Clones

Plasmid DNA was released from the cells and purified using the REAL Prep 96 plasmid kit (Catalog #26173, QIAGEN). This kit enabled the simultaneous purification of 96 samples in a 96-well block using multi-channel reagent dispensers. The recommended protocol was employed except for the following changes: 1) the bacteria were cultured in 1 ml of sterile TERRIFIC BROTH (Catalog #22711, GIBCO/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, *J. Mol. Biol.* 94:441f), using a MICROLAB 2200 (Hamilton) in combination with a DNA ENGINE thermal cyclers (PTC200 from MJ Research) and ABI PRISM 377 DNA Sequencing systems (PE Biosystems).

III Homology Searching of cDNA Clones and Their Deduced Proteins

After the reading frame was determined, the nucleotide sequences of the Sequence Listing as well as the amino acid sequences deduced from them were used as query sequences against databases such as GenBank, SwissProt, BLOCKS, and Pima II. These databases, which contain previously identified and annotated sequences, were searched for regions of homology (similarity) using BLAST, which stands for Basic Local Alignment Search Tool (Altschul (1993) supra, Altschul (1990) supra).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith et al. (1992, *Protein Engineering* 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach, as detailed in Karlin et al. (supra) and incorporated herein by reference, searched for matches between a query sequence and a database sequence. BLAST evaluated the statistical significance of any matches found, and reported only those matches that satisfy the user-selected threshold of significance. In this application, threshold was set at 10–25 for nucleotides and $10^{-14}$ for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, F. M. et al. supra, ch. 4 and 16.)

Analogous computer techniques applying BLAST are used to search for identical or related molecules in nucleotide databases such as GenBank or LIFESEQ database (Incyte Genomics, Palo Alto, Calif.). This analysis is much faster than multiple membrane-based hybridizations. In addition, the sensitivity of the computer search can be modified to determine whether any particular match is categorized as exact or homologous.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HAPA occurs. Abundance and percent abundance are also reported. Abundance directly reflects the number of times a particular transcript is represented in a cDNA library, and percent abundance is abundance divided by the total number of sequences examined in the cDNA library.

V. Extension of HAPA Encoding Polynucleotides

The nucleic acid sequence of Incyte Clone 3128715 was used to design oligonucleotide primers for extending a partial nucleotide sequence to full length. One primer was synthesized to initiate extension of an anti sense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 software (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (PE Biosystems) and thoroughly mixing the enzyme and reaction mix. PCR was performed using the DNA ENGINE thermal cycler (PTC200; M.J. Research), beginning with 40 pmol of each primer and the recommended concentrations of all other components of the kit, with the following parameters:

| Step 1  | 94° C. for 1 min (initial denaturation) |
|---------|------------------------------------------|
| Step 2  | 65° C. for 1 min |
| Step 3  | 68° C. for 6 min |
| Step 4  | 94° C. for 15 sec |
| Step 5  | 65° C. for 1 min |
| Step 6  | 68° C. for 7 min |
| Step 7  | Repeat steps 4 through 6 for an additional 15 cycles |
| Step 8  | 94° C. for 15 sec |
| Step 9  | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using a QIAQUICK kit (QIAGEN), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent *E. coli* cells (in 40 μl of appropriate media) were transformed with 3 μl of ligation mixture and cultured in 80 μl of SOC medium. (See, e.g., Sambrook, supra, Appendix A, p. 2.) After incubation for one hour at 37° C., the *E. coli* mixture was plated on Luria Bertani (LB) agar (See, e.g., Sambrook, supra, Appendix A, p. 1) containing 2xCarb. The following day, several colonies were randomly picked from each plate and cultured in 150 μl of liquid LB/2xCarb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3x) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 μCi of [γ-$^{32}$P] adenosine triphosphate (Amersham Pharmacia Biotech), and T4 polynucleotide kinase (NEN Life Sciences Products, Boston, Mass.). The labeled oligonucleotides are substantially purified using a SEPHADEX G-25 superfine resin column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba 1, or Pvu II (NEN Life Sciences Products).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1xsaline sodium citrate and 0.5% sodium dodecyl sulfate. After XOMAT AR film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using or thermal, UV, mechanical, or chemical bonding procedures, or a vacuum system. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

In another alternative, full-length cDNAs or Expressed Sequence Tags (ESTs) comprise the elements of the microarray. Full-length cDNAs or ESTs corresponding to one of the nucleotide sequences of the present invention, or selected at random from a cDNA library relevent to the present invention, are arranged on an appropriate substrate, e.g., a glass slide. The cDNA is fixed to the slide using, e.g., U.V. cross-linking followed, by thermal and chemical and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

Probe sequences for microarrays may be selected by screening a large number of clones from a variety of cDNA libraries in order to find sequences with conserved protein motifs common to genes coding for signal sequence containing polypeptides. In one embodiment, sequences identified from cDNA libraries, are analyzed to identify those gene sequences with conserved protein motifs using an appropriate analysis program, e.g., the Block 2 Bioanalysis Program (Incyte Genomics). This motif analysis program, based on sequence information contained in the Swiss-Prot Database and PROSITE, is a method of determining the function of uncharacterized proteins translated from genomic or cDNA sequences. (See, e.g., Bairoch, A. et al. (1997) Nucleic Acids Res. 25:217–221; and Attwood, T. K. et al. (1997) J. Chem. Inf. Comput. Sci. 37:417–424.) PROSITE may be used to identify functional or structural domains that cannot be detected using conserved motifs due to extreme sequence divergence. The method is based on weight matrices. Motifs identified by this method are then calibrated against the SWISS-PROT database in order to obtain a measure of the chance distribution of the matches.

In another embodiment, Hidden Markov models (HMMs) may be used to find shared motifs, specifically consensus sequences. (See, e.g., Pearson, W. R. and D. J. Lipman (1988) Proc. Natl. Acad. Sci. 85:2444–2448; and Smith, T. F. and M. S. Waterman (1981) J. Mol. Biol. 147:195–197.) HMMs were initially developed to examine speech recognition patterns, but are now being used in a biological context to analyze protein and nucleic acid sequences as well as to model protein structure. (See, e.g., Krogh, A. et al. (1994) J. Mol. Biol. 235:1501–1531; and Collin, M. et al. (1993) Protein Sci. 2:305–314.) HMMs have a formal probabilistic basis and use position-specific scores for amino acids or nucleotides. The algorithm continues to incorporate information from newly identified sequences to increase its motif analysis capabilities.

VIII. Complementary Polynucleotides

Sequences complementary to the HAPA-encoding sequences, or any parts thereof, are used to detect, decrease, or inhibit expression of naturally occurring HAPA. Although use of oligonucleotides comprising from about 15 to 30 base pairs is described, essentially the same procedure is used with smaller or with larger sequence fragments. Appropriate oligonucleotides are designed using OLIGO 4.06 software and the coding sequence of HAPA. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HAPA-encoding transcript.

IX. Expression of HAPA

Expression of HAPA is accomplished by subcloning the cDNA into an appropriate vector and transforming the vector into host cells. This vector contains an appropriate promoter, e.g., β-galactosidase upstream of the cloning site, operably associated with the cDNA of interest. (See, e.g., Sambrook, supra, pp. 404–433; and Rosenberg, M. et al. (1983) Methods Enzymol. 101:123–138.)

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of HAPA into bacterial growth media which can be used directly in the following assay for activity.

X. Demonstration of HAPA Activity

The aminotransferase, HAPA, catalyze the transfer of an alpha-amino acid to an alpha-keto acid. The activity of the purified enzyme HAPA toward various amino and oxo acid substrates is determined under single turnover conditions by monitoring the changes in the UV/VIS absorption spectrum of the enzyme-bound cofactor. The reactions are conducted at 25 ° C. in 50 mM 4-methylmorpholine, pH 7.5, containing 9 uM (subunit concentration) AspAT and the substrate. The half-reaction from amino acid to oxo acid is followed by measuring the decrease in absorbance at 360 nm and the increase in absorbance at 330 nm due to the conversion of enzyme-bound pyridoxal 5'-phosphate to pyridoxamine 5'-phosphate; the reverse half-reaction is followed in an analogous manner. The PMP form of the enzymes is prepared by incubation of the PLP form with 1 mM PMP and 5 mM cysteine sulfinate for 30 minutes at 25 ° C. in the dark followed by SEPHADEX G-25 chromatography. The reactions are followed with a Beckman 7400 DU spectrophotometer. With rapidly reacting substrates, a stopped-flow apparatus (a pbp-Spectra Kinetic Monochrometer 05-109 from Applied Photophysics) with a cuvette of 1-cm path length and a dead time of 2 ms is used. Steady-state aspartate aminotransferase activity is measured in a coupled assay with malate dehydrogenase in 50 mM 4-methylmorpholine, pH 7.5, at 25 ° C. in the presence of 20 mM 2-oxoglutarate plus 20 mM or 150 mM L-aspartate for wild-type enzyme or mutant AspATs, respectively.

XI. Production of HAPA Specific Antibodies

HAPA substantially purified using PAGE electrophoresis (see, e.g., Harrington, M. G. (1990) Methods Enzymol. 182:488–495), or other purification techniques, is used to immunize rabbits and to produce antibodies using standard protocols. The HAPA amino acid sequence is analyzed using LASERGENE software (DNASTAR Inc) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel et al. supra, ch. 11.)

Typically, the oligopeptides are 15 residues in length, and are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel et al. supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring HAPA Using Specific Antibodies

Naturally occurring or recombinant HAPA is substantially purified by immunoaffinity chromatography using antibodies specific for HAPA. An immunoaffinity column is constructed by covalently coupling anti-HAPA antibody to an activated chromatographic resin, such as CNBr-activated SEPHAROSE (Amersham Pharmacia Biotech). After the coupling, the resin is blocked and washed according to the manufacturer's instructions.

Media containing HAPA are passed over the immunoaffinity column, and the column is washed under conditions that allow the preferential absorbance of HAPA (e.g., high ionic strength buffers in the presence of detergent). The column is eluted under conditions that disrupt antibody/HAPA binding (e.g., a buffer of pH 2 to pH 3, or a high concentration of a chaotrope, such as urea or thiocyanate ion), and HAPA is collected.

XIII. Identification of Molecules Which Interact with HAPA

HAPA, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled HAPA, washed, and any wells with labeled HAPA complex are assayed. Data obtained using different concentrations of HAPA are used to calculate values for the number, affinity, and association of HAPA with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A purified polypeptide comprising an amino acid sequence selected from the group consisting of:
   a) an amino acid sequence of SEQ ID NO:1,
   b) an amino acid sequence having at least 90% sequence identity to the sequence of SEQ ID NO:1, and which retains beta-alanine-pyruvate aminotransferase activity, and
   c) a biologically-active fragment of the amino acid sequence of SEQ ID NO:1.

2. An isolated polypeptide of claim 1, having a sequence of SEQ ID NO:1.

3. A composition comprising an effective amount of a polypeptide of claim 1 and a pharmaceutically acceptable excipient.

4. A composition of claim 3, wherein the polypeptide has the sequence of SEQ ID NO:1.

5. A method for screening a compound for effectiveness as an agonist of a polypeptide of claim 1, the method comprising:
   a) exposing a sample comprising a polypeptide of claim 1 to a compound, and
   b) detecting agonist activity in the sample.

6. A method for screening a compound for effectiveness as an antagonist of a polypeptide of claim 1, the method comprising:
   a) exposing a sample comprising a polypeptide of claim 1 to a compound, and
   b) detecting antagonist activity in the sample.

7. A method for using a polypeptide for screening a plurality of molecules or compounds for a molecule or compound which specifically binds the polypeptide, the method comprising:

a) combining the polypeptide of claim 1 with a plurality of molecules or compounds under conditions to allow specific binding, and b) detecting specific binding between the polypeptide and the molecule or compound, thereby identifying a molecule or compound that specifically binds the polypeptide.

8. A method of using a polypeptide to purify a molecule or compound which specifically binds the polypeptide from a sample, the method comprising:

a) combining the polypeptide of claim 1 with a sample under conditions to allow specific binding;

b) recovering the bound polypeptide; and c) separating the polypeptide from the molecule or compound, thereby obtaining purified molecule or compound.

9. An isolated immunogenic fragment of the amino acid sequence of SEQ ID NO:1.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 450 amino acids
      (B) TYPE: amino acid
      (C) STRANDEDNESS: single
      (D) TOPOLOGY: linear (vii) IMMEDIATE SOURCE:
      (A) LIBRARY: LUNGTUT12
      (B) CLONE: 3128715

(xi) SEQUENCE DESCRIPTION: SEQ ID NO: 1:

```
Met Ala Ala Asp Gln Arg Pro Lys Ala Asp Thr Leu Ala Leu Arg Gln
  1               5                  10                  15

Arg Leu Ile Ser Ser Ser Cys Arg Leu Phe Phe Pro Glu Asp Pro Val
                 20                  25                  30

Lys Ile Val Arg Ala Gln Gly Gln Tyr Met Tyr Asp Glu Gln Gly Ala
                 35                  40                  45

Glu Tyr Ile Asp Cys Ile Ser Asn Val Ala His Val Gly His Cys His
     50                  55                  60

Pro Leu Val Val Gln Ala Ala His Glu Gln Asn Gln Val Leu Asn Thr
 65                  70                  75                  80

Asn Ser Arg Tyr Leu His Asp Asn Ile Val Asp Tyr Ala Gln Arg Leu
                 85                  90                  95

Ser Glu Thr Leu Pro Glu Gln Leu Cys Val Phe Tyr Phe Leu Asn Ser
                100                 105                 110

Gly Ser Glu Ala Asn Asp Leu Ala Leu Arg Leu Ala Arg His Tyr Thr
                115                 120                 125

Gly His Gln Asp Val Val Leu Asp His Ala Tyr His Gly His Leu
                130                 135                 140

Ser Ser Leu Ile Asp Ile Ser Pro Tyr Lys Phe Arg Asn Leu Asp Gly
145                 150                 155                 160

Gln Lys Glu Trp Val His Val Ala Pro Leu Pro Asp Thr Tyr Arg Gly
                165                 170                 175

Pro Tyr Arg Glu Asp His Pro Asn Pro Ala Met Ala Tyr Ala Asn Glu
                180                 185                 190

Val Lys Arg Val Val Ser Ser Ala Gln Glu Lys Gly Arg Lys Ile Ala
                195                 200                 205

Ala Phe Phe Ala Glu Ser Leu Pro Ser Val Gly Gln Ile Ile Pro
                210                 215                 220

Pro Ala Gly Tyr Phe Ser Gln Val Ala Glu His Ile Arg Lys Ala Gly
225                 230                 235                 240

Gly Val Phe Val Ala Asp Glu Ile Gln Val Gly Phe Gly Arg Val Gly
                245                 250                 255

Lys His Phe Trp Ala Phe Gln Leu Gln Gly Lys Asp Phe Val Pro Asp
                260                 265                 270

Ile Val Thr Met Gly Lys Ser Ile Gly Asn Gly His Pro Val Ala Cys
                275                 280                 285

Val Ala Ala Thr Gln Pro Val Ala Arg Ala Phe Glu Ala Thr Gly Val
                290                 295                 300
```

```
Glu Tyr Phe Asn Thr Phe Gly Gly Ser Pro Val Ser Cys Ala Val Gly
305                 310                 315                 320

Leu Ala Val Leu Asn Val Leu Glu Lys Glu Gln Leu Gln Asp His Ala
                325                 330                 335

Thr Ser Val Gly Ser Phe Leu Met Gln Leu Leu Gly Gln Gln Lys Ile
                340                 345                 350

Lys His Pro Ile Val Gly Asp Val Arg Gly Val Gly Leu Phe Ile Gly
                355                 360                 365

Val Asp Leu Ile Lys Asp Glu Ala Thr Arg Thr Pro Ala Thr Glu Glu
370                 375                 380

Ala Ala Tyr Leu Val Ser Arg Leu Lys Glu Asn Tyr Val Leu Leu Ser
385                 390                 395                 400

Thr Asp Gly Pro Gly Arg Asn Ile Leu Lys Phe Lys Pro Pro Met Cys
                405                 410                 415

Phe Ser Leu Asp Asn Ala Arg Gln Val Val Ala Lys Leu Asp Ala Ile
                420                 425                 430

Leu Thr Asp Met Glu Glu Lys Val Arg Ser Cys Glu Thr Leu Arg Leu
                435                 440                 445

Gln Pro
    450

(2) INFORMATION FOR SEQ ID NO: 2:

(i) SEQUENCE CHARACTERISTICS:
        (A) LENGTH: 1786 base pairs
        (B) TYPE: nucleic acid
        (C) STRANDEDNESS: single
        (D) TOPOLOGY: linear (vii) IMMEDIATE SOURCE:
        (A) LIBRARY: LUNGTUT12
        (B) CLONE: 3128715

(xi) SEQUENCE DESCRIPTION: SEQ ID NO: 2:

CGCCCGCGCG GCGACGTCTC CGCGAGGCGT CACGGCACCG ACTGACGGCC ACCCACCAT        60

GCCGCAGACC AGCGCCCGAA GGCCGACACC CTGGCCCTGA GGCAACGGCT CATCAGCT       120

TCCTGCAGAC TCTTTTTTCC CGAGGATCCT GTTAAGATTG TCCGGGCCCA AGGGCAGT       180

ATGTACGATG AACAGGGGGC AGAATACATC GATTGCATCA GCAATGTGGC GCACGTTG       240

CACTGCCACC CTCTCGTGGT CCAAGCAGCA CATGAGCAGA ACCAGGTGCT CAACACCA       300

AGCCGGTACC TGCATGACAA CATCGTGGAC TATGCGCAGA GGCTGTCAGA GACCCTGC       360

GAGCAGCTCT GTGTGTTCTA TTTCCTGAAT TCTGGGTCAG AAGCCAATGA CCTGGCCC       420

AGGCTGGCTC GCCACTACAC GGGACACCAG GACGTGGTGG TATTAGATCA TGCGTATC       480

GGCCACCTGA GCTCCCTGAT TGACATCAGT CCCTACAAGT TCCGCAACCT GGATGGCC       540

AAGGAGTGGG TCCACGTGGC ACCTCTCCCA GACACCTACC GGGGCCCCTA CCGGGAGG       600

CACCCCAACC CAGCTATGGC CTATGCCAAC GAGGTGAAAC GTGTGGTCAG CAGTGCAC       660

GAGAAGGGCA GGAAGATTGC AGCCTTCTTC GCTGAGTCTC TGCCCAGTGT GGGAGGGC       720

ATCATTCCCC CTGCTGGCTA CTTCTCCCAA GTGGCAGAGC ACATCCGCAA GGCCGGAG       780

GTCTTTGTTG CAGATGAGAT CCAGGTTGGC TTTGGCCGGG TAGGCAAGCA CTTCTGGG       840

TTCCAGCTCC AGGGAAAAGA CTTCGTCCCT GACATCGTCA CCATGGGCAA GTCCATTG       900

AACGCCACCC TGTTGCCCTG CGTGGCCGCA ACCCAGCCTG TGGCGAGGGC ATTTGAAG       960

ACCGGCGTTG AGTACTTCAA CACGTTTGGG GGCAGCCCAG TGTCCTGCGC TGTGGGG      1020
```

```
                                                           -continued

GCCGTCCTGA ATGTCTTGGA GAAGGAGCAG CTCCAGGATC ATGCCACCAG TGTAGGC        1080

TTCCTGATGC AGCTCCTCGG GCAGCAAAAA ATCAAACATC CCATCGTCGG GGATGTC        1140

GGTGTTGGGC TCTTCATTGG TGTGGATCTG ATCAAAGATG AGGCCACAAG GACACCA        1200

ACTGAAGAGG CTGCCTACTT GGTATCAAGG CTGAAGGAGA ACTACGTTTT GCTGAGC        1260

GATGGCCCTG GGAGGAACAT CCTGAAGTTT AAGCCCCCAA TGTGCTTCAG CCTGGAC        1320

GCACGGCAGG TGGTGGCAAA GCTGGATGCC ATTCTGACTG ACATGGAAGA GAAGGTG        1380

AGTTGTGAAA CGCTGAGGCT CCAGCCCTAA GCCAGCCCTG CTCTGCCTAA GTGTACT        1440

GAAGAAACTC ATCTCATCCA AATACACGCT ATTGAGAAGG CGAGCCTGAC CTCCCTC        1500

CAGATAAAGT CAGCTTTCAG AGGCTCAGGG TGGGGGGGCC TGCCCGAGGC CATAATG        1560

CCCACCCCCT CCTCCTAACC ACTGGTCTGT TGGAATAACC CAGATGTCTG CATCCCC        1620

AGTCAGTCAA TTTCCTTTCT GTCCACTGGG GGTGGAATGG GGTAGGGTGG GATACTT        1680

AGTGCTCCTG CTTAAATAAA TTAGACCAGA CCAGTGTATT TCTAAAGAAA ATCCTGA        1740

GCACACCCAT TAAAAATAGT ACATTTTACA GTGAAAAAAA AAAAA                     1786

(2) INFORMATION FOR SEQ ID NO: 3:

(i) SEQUENCE CHARACTERISTICS:
         (A) LENGTH: 512 amino acids
         (B) TYPE: amino acid
         (C) STRANDEDNESS: single
         (D) TOPOLOGY: linear (vii) IMMEDIATE SOURCE:
         (A) LIBRARY: GenBank
         (B) CLONE: 1944136

(xi) SEQUENCE DESCRIPTION: SEQ ID NO: 3:

Met Ser Leu Ala Trp Arg Thr Leu Gln Lys Ala Phe Tyr Leu Glu Thr
1               5                   10                  15

Ser Leu Arg Ile Leu Gln Met Arg Pro Ser Leu Ser Cys Ala Ser Arg
            20                  25                  30

Ile Tyr Val Pro Lys Leu Thr Leu His Thr Lys His Asn Met Pro Pro
        35                  40                  45

Cys Asp Phe Ser Pro Glu Lys Tyr Gln Ser Leu Ala Tyr Asn His Val
    50                  55                  60

Leu Glu Ile His Lys Gln His Leu Ser Pro Val Asn Thr Ala Tyr Phe
65                  70                  75                  80

Gln Lys Pro Leu Leu Leu His Gln Gly His Met Glu Trp Leu Phe Asp
                85                  90                  95

Ser Glu Gly Asn Arg Tyr Leu Asp Phe Phe Ser Gly Ile Val Thr Val
            100                 105                 110

Gly Val Gly His Cys His Pro Lys Val Thr Ala Val Ala Lys Lys Gln
        115                 120                 125

Met Asp Arg Leu Trp His Thr Ser Ser Val Phe Phe His Ser Pro Met
    130                 135                 140

His Glu Tyr Ala Glu Arg Leu Ser Ala Leu Leu Pro Glu Pro Leu Lys
145                 150                 155                 160

Val Ile Phe Leu Val Asn Ser Gly Ser Glu Ala Asn Asp Leu Ala Met
                165                 170                 175

Val Met Ala Arg Ala Tyr Ser Asn His Thr Asp Ile Ile Ser Phe Arg
            180                 185                 190

Gly Ala Tyr His Gly Cys Ser Pro Tyr Thr Leu Gly Leu Thr Asn Val
        195                 200                 205
```

-continued

```
Gly Ile Tyr Lys Met Lys Val Pro Ser Thr Ile Ala Cys Gln Ser Thr
        210                 215                 220

Met Cys Pro Asp Val Phe Arg Gly Pro Trp Gly Ser His Cys Arg
225                     230                 235                 240

Asp Ser Pro Val Gln Thr Val Arg Lys Cys Ser Cys Ala Pro Asp Gly
                245                 250                 255

Cys Gln Ala Lys Glu Arg Tyr Ile Glu Gln Phe Lys Asp Thr Leu Asn
                260                 265                 270

Thr Ser Val Ala Thr Ser Ile Ala Gly Phe Phe Ala Glu Pro Ile Gln
                275                 280                 285

Gly Val Asn Gly Val Val Gln Tyr Pro Lys Glu Phe Leu Lys Glu Ala
        290                 295                 300

Phe Ala Leu Val Arg Glu Arg Gly Gly Val Cys Ile Ala Asp Glu Val
305                     310                 315                 320

Gln Thr Gly Phe Gly Arg Leu Gly Ser His Phe Trp Gly Phe Gln Thr
                325                 330                 335

His Asp Thr Met Pro Asp Ile Val Thr Met Ala Lys Gly Ile Gly Asn
                340                 345                 350

Gly Phe Pro Met Ala Ala Val Val Thr Thr Pro Glu Ile Ala Ser Ser
                355                 360                 365

Leu Ala Lys His Leu His His Phe Ser Thr Phe Gly Gly Ser Pro Leu
        370                 375                 380

Ala Cys Ala Ile Gly Ser Ala Val Leu Glu Val Ile Glu Glu Glu Asn
385                     390                 395                 400

Leu Gln Arg Asn Ser Gln Glu Val Gly Thr Tyr Met Leu Leu Lys Phe
                405                 410                 415

Ala Lys Leu Arg Asp Glu Phe Asp Ile Val Gly Asp Val Arg Gly Lys
                420                 425                 430

Gly Leu Met Val Gly Ile Glu Met Val Gln Asp Lys Ile Ser Arg Gln
                435                 440                 445

Pro Leu Pro Lys Thr Glu Val Asn Gln Ile His Glu Asp Cys Lys Asp
        450                 455                 460

Met Gly Leu Leu Val Gly Arg Gly Gly Asn Phe Ser Gln Thr Phe Arg
465                     470                 475                 480

Ile Ala Pro Pro Met Arg Val Thr Lys Leu Glu Val Asp Phe Ala Phe
                485                 490                 495

Glu Val Phe Arg Ser Ala Leu Thr Gln His Met Glu Arg Arg Ala Lys
                500                 505                 510
```